United States Patent
Guracar

(10) Patent No.: US 9,084,576 B2
(45) Date of Patent: Jul. 21, 2015

(54) AUTOMATIC DOPPLER GATE POSITIONING IN SPECTRAL DOPPLER ULTRASOUND IMAGING

(75) Inventor: Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 62 days.

(21) Appl. No.: 13/548,561

(22) Filed: Jul. 13, 2012

(65) Prior Publication Data

US 2014/0018680 A1 Jan. 16, 2014

(51) Int. Cl.
*A61B 8/00* (2006.01)
*A61B 8/08* (2006.01)
*G03B 42/06* (2006.01)
*G01S 7/52* (2006.01)

(52) U.S. Cl.
CPC ............... *A61B 8/463* (2013.01); *A61B 8/488* (2013.01); *A61B 8/5276* (2013.01); *G01S 7/52066* (2013.01); *G01S 7/52085* (2013.01); *G03B 42/06* (2013.01)

(58) Field of Classification Search
CPC ...... A61B 8/463; A61B 8/488; A61B 8/5276; G03B 42/06; G01S 7/52066; G01S 7/52085
USPC .................................................. 600/437–469
See application file for complete search history.

(56) References Cited

U.S. PATENT DOCUMENTS

| 3,032,834 | A  | * | 5/1962  | Carlson ........................ 49/141 |
| 5,724,974 | A  | * | 3/1998  | Goodsell et al. ............... 600/453 |
| 5,785,655 | A  | * | 7/1998  | Goodsell et al. ............... 600/441 |
| 6,322,509 | B1 | * | 11/2001 | Pan et al. ....................... 600/443 |
| 6,423,006 | B1 | * | 7/2002  | Banjanin ....................... 600/453 |
| 7,578,792 | B2 | * | 8/2009  | Lee et al. ....................... 600/453 |
| 8,092,388 | B2 | * | 1/2012  | Park et al. ..................... 600/450 |
| 2007/0161898 | A1 | * | 7/2007  | Hao et al. ..................... 600/443 |
| 2010/0022884 | A1 | * | 1/2010  | Ustuner et al. ................ 600/453 |

OTHER PUBLICATIONS

U.S. Appl. No. 13/032,834, filed Feb. 23, 2011.

* cited by examiner

*Primary Examiner* — Sanjay Cattungal

(57) ABSTRACT

A Doppler gate is automatically positioned in spectral Doppler ultrasound imaging. Samples acquired for multiple PW Doppler gates are used for B-mode and/or F-mode detection over time without interleaving transmissions for the PW Doppler. The B-mode and/or F-mode information are used to track gate placement. Alternatively or additionally, characteristics spectra from different gate locations are used to select a gate location. Either tracking may be used to change the locations sampled and/or beam characteristics, such as centering the locations and beam focus on the selected gate location.

20 Claims, 3 Drawing Sheets

AUTOMATIC DOPPLER GATE POSITIONING IN SPECTRAL DOPPLER ULTRASOUND IMAGING

BACKGROUND

The present invention relates to pulsed wave (PW) spectral Doppler ultrasound. Spectral Doppler ultrasound imaging provides an image of velocities (vertical axis) values modulated by energy as a function of time (horizontal axis). This spectrum may be used for studying fluid flow or tissue motion within a patient. By transmitting a plurality of pulses at a single gate location, a spectral Doppler response is generated in response to received echo signals. The frequency spectrum of the object's motion or flow for a single spatial region is estimated and displayed as a function of time.

Sonographers manually adjust the gate location, gate size, transmit frequency and other spectral Doppler imaging control parameters in order to acquire a desirable image. The gate placement is assisted by display of a 2D B-mode image of the anatomy of interest. Some processes have been proposed for automatic placement of the spectral Doppler gate using B-mode or color Doppler (F-mode) information. However, obtaining the B-mode or F-mode information interrupts the acquisition of the relatively high pulse repetition frequency PW Doppler. A brief interruption (e.g., 10-20 ms) allows at least a portion of the two or three-dimensional B-mode or F-mode data to be acquired. This produces gaps in the PW Doppler measurement. Depending on the temporal characteristics of the PW Doppler waveform due to flow dynamics, vital information may be lost during this time interval.

BRIEF SUMMARY

By way of introduction, the preferred embodiments described below include methods, systems, computer readable media, and instructions for positioning a Doppler gate in spectral Doppler ultrasound imaging. Samples acquired for multiple PW Doppler gates are used for B-mode and/or F-mode detection over time without interleaving transmissions from the PW Doppler. The B-mode and/or F-mode information are used to track gate placement. Alternatively or additionally, characteristics of spectra from different gate locations are used to select a gate location. Either positioning may be used to change the locations sampled and/or beam characteristics, such as centering the locations and beam focus on the selected gate location.

In a first aspect, a method is provided for positioning a Doppler gate in spectral Doppler ultrasound imaging. Transmit beams are transmitted repetitively from a transducer array. In response to the transmitting, signals from different receive locations are repetitively received. B-mode information representing the different receive locations at different times is detected from at least some of the signals. The Doppler gate location is tracked with the B-mode information. A first spectrum for the tracked Doppler gate location is estimated from the signals for the tracked Doppler gate location. An image is displayed as a function of the first spectrum.

In a second aspect, a non-transitory computer readable storage medium has stored therein data representing instructions executable by a programmed processor for positioning a Doppler gate in spectral Doppler ultrasound imaging. The storage medium includes instructions for receiving signals over time for each a plurality of spaced apart locations, performing spectral analysis of the signals separately for each of the spaced apart locations, the spectral analysis providing spectra for each of the spaced apart locations, detecting a characteristic of each spectra from the spaced apart locations, setting a Doppler gate location to one of the spaced apart locations as a function of the characteristic of each spectrum, and updating a distribution of the spaced apart locations as a function of the set Doppler gate location so that a center of the distribution is at the set Doppler gate location.

In a third aspect, a system is provided for positioning a Doppler gate in spectral Doppler ultrasound imaging. A transmit beamformer is operable to transmit beams. A receive beamformer is operable to form a plurality of spaced apart receive beams in response to each of the transmit beams, each of the receive beams sampled at a plurality of depths. A processor is configured to set a location of the Doppler gate as a function of the sampled receive beams and to control the transmit beamformer to center the transmit beams and spacing of the sampling of the receive beams on the location.

In a fourth aspect, a non-transitory computer readable storage medium has stored therein data representing instructions executable by a programmed processor for positioning a Doppler gate in spectral Doppler ultrasound imaging. The storage medium includes instructions for receiving signals over time for each a plurality of spaced apart locations, detecting B-mode information for different times from at least some of the signals, tracking a location over time with the B-mode information, updating the spaced apart locations as a function of the tracked location, performing spectral analysis of the signals separately for each of the spaced apart locations, the spectral analysis providing spectra for each of the spaced apart locations, detecting a characteristic of each spectra from the spaced apart locations, and setting a Doppler gate location to one of the spaced apart locations as a function of the characteristic of each spectra.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
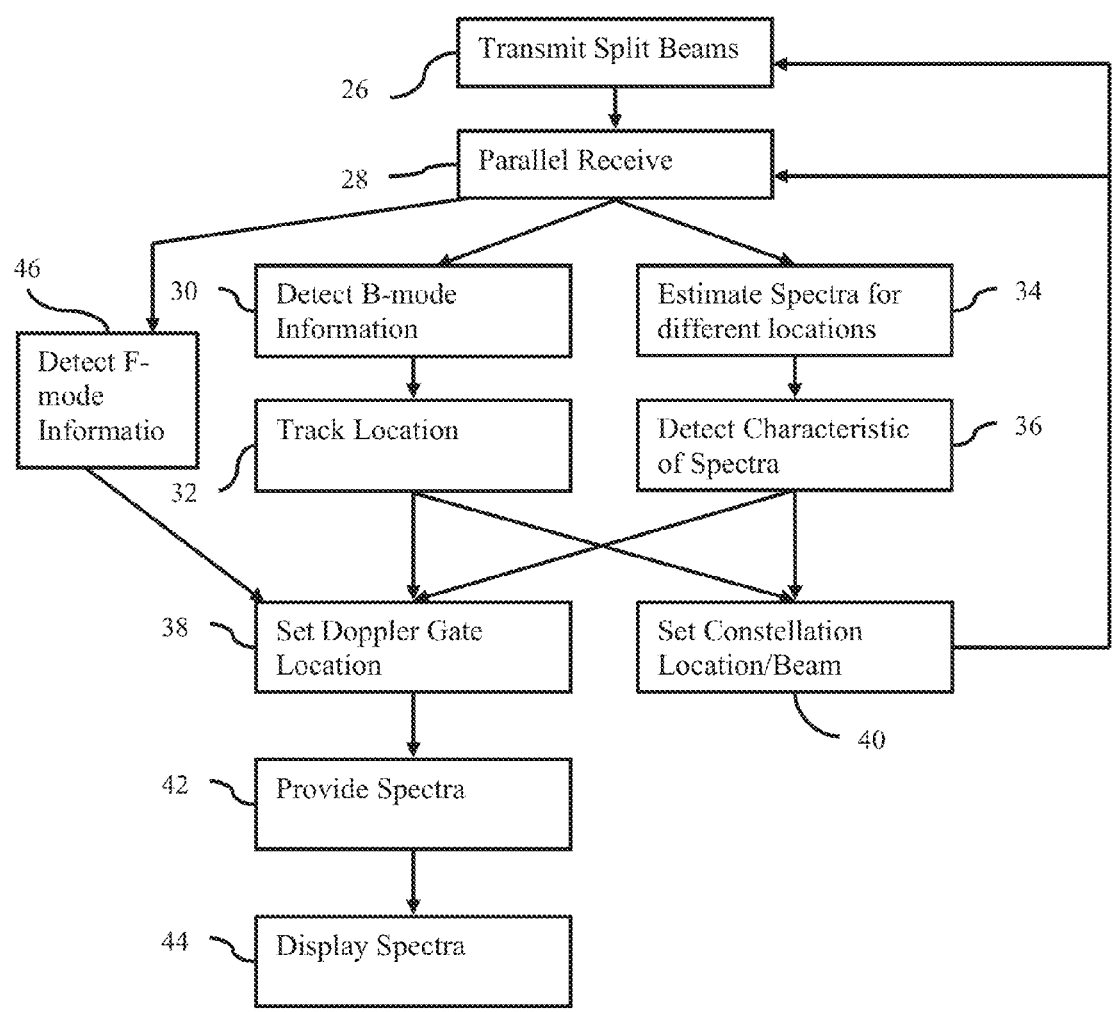
FIG. 1 is a flow chart diagram of one embodiment of a method for positioning a Doppler gate in spectral Doppler ultrasound imaging.

Automatic Doppler gate placement is provided in ultrasonic blood flow measurement, such as for cardiac valve applications, or in tissue motion measurement. Once the gate has been placed, continuous positioning ensures that the gate position is maintained even in the presence of motion from the patient (e.g., from breathing) or the transducer position (e.g., from the sonographer moving). The continuous monitoring and/or positioning of the gate occurs without interrupting PW spectral Doppler acquisition for other types of scanning.

Multi-transmit and/or receive beam capability is used to acquire a constellation of Doppler gates in a region near the optimal gate position. PW Doppler gate position and/or beamforming are based on simultaneous acquisition of data for multiple spectral Doppler gates. Multiple gates may be located along an ultrasound beam (multiple range gates). Parallel receive beamforming allows multiple gates in lateral and/or elevation directions within the area covered by a transmit beam or beams. Using split beam (parallel transmit beams), two or more spatially distinct regions may be interrogated.

The data acquired for the constellation represents the region or regions. The data acquired at the Doppler gates may also be used for B-mode and/or F-mode detection. The spectral Doppler signals themselves and/or the B-mode/color region of the constellation are used for positioning. As the target moves because of patient or transducer motion, the optimal gate placement is maintained. The detection and tracking of motion only requires a constellation of Doppler gates to be acquired without interrupting the PW Doppler acquisition and while maintaining the highest temporal sampling quality.

In one embodiment, the multigate constellation acquisition provides data for concurrently acquired B-mode and/or F-mode images in addition to the PW Doppler information. The B-mode and/or F-mode images are used for continuous tracking. The optimal gate position is maintained by adjusting the location used for estimating spectra.

In another embodiment, a Doppler strip is generated for each location of the multigate constellation. Each strip is analyzed and compared with the others to determine the best gate position.

Both approaches may be used together. For example, the B-mode tracking is used to center the constellation of gates. The spectral analysis is used to select the Doppler gate location from among the constellation of gates.

In either approach, lateral and/or elevation transmit beam profiles and transmit focus depth may be adjusted to be centered at the optimal gate position. The constellation may be adjusted to be centered at the optimal gate position. The transmit line and/or transmit focal depth of the center of the gate constellation is moved in response to motion. The highest transmit power and best beam profile characteristics may be centered on a region of acquired Doppler gates, maintaining the best characteristics while tracking motion.

Where there is loss of tracking or excessive movement is detected, the system may reset. A new image-based gate placement cycle is automatically initiated instead of continuing to track or position.

FIG. 1 shows method for positioning a Doppler gate in spectral Doppler ultrasound imaging. The method is implemented on the system 10 of FIG. 7 or a different system. The acts are performed in the order shown, but other orders are possible. Acts 30 and 32 are performed sequentially or simultaneously with acts 34 and 36. Acts 38 and 40 are performed simultaneously or sequentially in any order. Act 42 may be performed before act 40. Other orders may be used.

Additional, different, or fewer acts may be provided. For example, acts 30 and 32 are not performed. As another example, acts 34 and 36 are not performed. In yet another example, act 46 is not performed. Acts 40 and/or 44 may not be performed. Various combinations may be used.

For positioning a PW Doppler gate, ultrasound samples or signals are obtained for a plurality of spatially distinct locations. The samples are obtained by transmitting beams in act 26. One or more transmit beams are transmitted at a given time. To cover a larger region, simultaneous transmit beams may be formed. Simultaneous formation of beams on different scan lines may be used. For example, two transmit beams are formed at different steering angles, from different origins on the transducer array, and/or from the transducer at different positions. The transmit beams are formed along different scan lines. In the near field and far field, the transmit beams may over lap. At the focal region some or no overlap is provided. The −6 dB or −10 dB edge of the transmit beams overlap or are separated by a region of lesser acoustic power from the transmit beams. Non-overlapping regions in the middle field, far field and/or near field may be used.

Two or more beams are transmitted substantially simultaneously. Substantially accounts for different delays or start of transmissions due to different foci or steering. Substantially provides for two beams to be transmitted within sufficient time of each other that at least a portion of a wavefront of one waveform is generated acoustically before the last of returned echoes for another wavefront are received at the transducer. The wavefronts from both beams may be transmitted by a majority of the elements of the transducer prior to any reception operation. Simultaneous transmission includes generating acoustic waveforms for one beam while also doing so for another beam, such as transmitting a waveform for one beam from one element while also transmitting a waveform for another beam from another element or the one element.

The split beams (e.g., substantially simultaneous transmit beams along different scan lines) are generated using any possible method. For example, different apertures are formed on the transducer array. Each aperture is for transmitting a different one or ones of the transmit beams. The apertures are unique or do not overlap, such as using right and left halves of the array for two different beams. The apertures may be neighboring sections, may be spatially interleaved (e.g., every other element for one aperture and the other elements for another aperture), or may overlap (e.g., one or more elements transmit waveforms for both beams). The different apertures produce spatially distinct transmit beams by application of a suitable delay and/or phasing pattern.

In another embodiment, the waveforms for two or more beams are applied to the same or overlapping apertures at a substantially simultaneous time. For each element, the electrical waveforms for the different beams are combined (e.g., summed) based on the separate delay and/or phasing and apodization profiles. The combined waveforms are transmitted from the elements of the aperture, forming the transmit beams substantially simultaneously.

For receive isolation or to limit contribution to received samples for one beam from another beam, different center frequencies, coding, or center frequencies and coding may be used for each beam. For example, frequency multiplexing is used. Two or more transmit pulses having different center frequencies are transmitted. Different delay profiles are used for the pulses at different frequencies so that two or more beams are created in parallel (temporally). For coding, any coding may be used, such as spread spectrum codes or orthogonal codes. Frequency-based codes, amplitude-based codes, phase-based codes, or combinations thereof may be used. In alternative embodiments, no coding or frequency difference is provided. The spatial differences in the transmit beams differentiate the receive signals.

In other embodiments, combinations of techniques for generating substantially simultaneous transmit beams may be used. For example, the aperture is split into two spatially overlapping groups. The groups transmit pulses having different center frequencies so that spatially distinct beams are generated that are separated in frequency.

In other embodiments, one transmit beam is formed at a given time. The transmit beam is formed with a sufficient beam width to allow receive beamformation along laterally and/or elevationally spaced receive scan lines. Plane wave, infinite focus, spread beam, or narrow beam with sufficient width may be used. Split or multi-beam may be used with such wide or diverging wavefront transmit beams.

For either the simultaneous beams or the single beam, the transmissions are repeated. The repetition allows reception of sufficient samples to perform spectral analysis.

In act 28, signals for a plurality of laterally spaced locations are received in response to each of the transmit beams. Receive beams are formed along a plurality (e.g., two or more, such as 32 or 64) of scan lines in response to each of the transmit beams. A plurality of scan lines and ranges along the scan lines may be sampled in response to the single transmission. Parallel receive beamforming is provided. The ultrasound samples are obtained at a substantially same time along a plurality of receive beams responsive to a same transmit beam. Other plane wave transmission and reception techniques may be used, such as applying a Fourier transform to electrical signals at each element to generate an array of values representing response at different locations.

Figure 3:
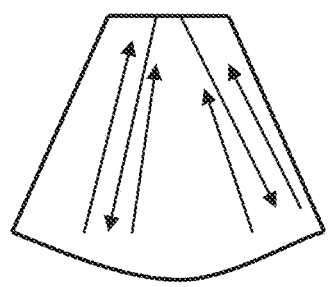
FIG. 3 is a graphical representation of example parallel beamforming in a region of interest.

FIG. 3 shows one embodiment where one transmission of split beams in act 26 is used to acquire a plurality of receive beams in act 28. While two receive beams are shown, a greater density may be provided, such as four, eight, sixteen, thirty two, sixty-four, or other number of receive beams per transmit beam. The transmit and receive beams intersect a region of interest.

The region of interest may be any size or shape. The region of interest defines the spatial locations for which spectra may be estimated. For example, at least one hundred locations are sampled for possible spectral analysis. The region may be contiguous or divided. Multiple regions may be scanned.

Any sampling density of locations may be used in the region of interest. The distribution of locations is a constellation of sample points for possible spectral analysis. The constellation may be a distribution in two or three dimensions. Symmetric or asymmetric distribution may be used, such as sampling in 64 lateral and elevation spaced locations and at 10 depth spaced locations.

The receive operation occurs repetitively in response to the transmitting. Signals from laterally and/or elevationally distinct receive locations within the transmit beams are received. By forming a plurality of receive beams in response to each of the transmit beams, signals for many receive locations are obtained substantially simultaneously. "Substantially" accounts for the acoustic travel time along a line in a field of view.

Samples for the same locations are acquired over time. Ultrasound samples are obtained over a period, such as acquiring five or more ultrasound samples for each spatial location. Any scan sequence and/or pulse repetition frequency may be used.

The PW Doppler gate is to be positioned at one of the sample locations of the constellation. Sufficient samples are obtained to estimate the spectra over time for any of the sample locations. Three different approaches may be used alone or in combination to position the PW Doppler gate for a spectral strip display at one of the sample locations. Acts 30 and 32 represent an approach using B-mode detection. Acts 34 and 36 represent an approach using spectral analysis. Act 46 represents an approach using F-mode detection. Other approaches may be used.

In act 30, B-mode information is generated. The B-mode information is generated from the PW Doppler samples. While the transmit and/or receive characteristics (e.g., frequency, number of cycles, F#, or aperture) may typically be different for PW Doppler and B-mode, samples acquired for PW Doppler may be used for B-mode detection. The transmit and/or receive characteristics may be compromised for both spectral analysis and B-mode detection or optimized for B-mode detection in other embodiments. The same data is used for both.

For spectral analysis, an ensemble of signals from a same location is acquired, such as five to twenty samples for each spectrum. The samples may be obtained in an ongoing manner such that a moving window (e.g., ensemble or flow sample count) with any step size (e.g., every sample or every third sample) is used to estimate a spectrum. The B-mode detection uses a single sample to estimate the intensity. One of the samples from a given ensemble is selected and used. To estimate B-mode at different times, signals from different times in the same or different ensemble are selected. B-mode information may be detected for each signal for a greatest temporal resolution. In other embodiments, less than all of the signals are used for B-mode detection, such as performing B-mode detection with every fifth sample.

Since signals are acquired for the constellation, the B-mode data is detected for the region of interest. The intensity from single samples of the signals for the different receive locations is detected. The detection is performed for different times. B-mode information generally represents return from tissue or other structure within the patient. By detecting over time, the tissue in the region of interest is detected at different times. As motion occurs, the tissue appears or does shift, rotate, compress, or expand. The B-mode information over time reflects the change.

In act 32, a location is tracked over time with the B-mode information. The location is a Doppler gate location. For example, the user places an initial Doppler gate. As another example, act 46 or acts 34 and 36 are used to initially place the Doppler gate. In another example, automatic placement using a prior B-mode scan (e.g., boundary or edge detection to place a gate in the center of an enclosed boundary) or other approach is used.

The location of the Doppler gate is tracked. In other embodiments, the location being tracked is the entire region of interest. Other locations may be tracked, such as a center of the region of interest or a sub-area or sub-volume of the region of interest.

The tracking detects a change of the location over time. The location may be at one coordinate at one time, but shift to be at another coordinate at another time. The coordinates are defined with respect to the scanning, such as with respect to the scan format from the ultrasound transducer. The location is relative to the patient. Data at different coordinates for different times may represent the same location.

For tracking the location, a kernel of B-mode information representing different spatial locations is used. Any size kernel may be provided, such as 9×9 or 12×12×12 neighborhood around the location or the entire region of interest. The entire region of interest may be used as the kernel.

The kernel is a reference set. The reference is for B-mode information at a first, selected, or given time. The reference may be updated, such as changing the reference over time. For example, the reference B-mode information is temporally adjacent to the most recently acquired B-mode information in a moving window. The reference B-mode information is updated each time another frame of B-mode information is detected. In another embodiment, the reference B-mode information is only updated once sufficient motion has occurred to change the constellation location and/or beam location (e.g., scan line shift) in act 40.

To track, the reference information is compared to the B-mode information from another time. Multiple comparisons are made between the B-mode information from two times. Different translation, rotations, and/or scales are attempted. The translation, rotation, and/or scale with the best or highest similarity indicate the motion or change in position between times. In one embodiment, just translation is tracked.

Any measure of similarity may be used. For example, a minimum sum of absolute differences is calculated. Cross-correlation or other measures may be used.

In another approach to determine positions for the Doppler gate over time, spectra are estimated for the different locations in act 34. Spectra are estimated for the receive locations. A spectrum is estimated for each of the spatially distinct locations. The spectra are estimated from the ultrasound samples from different depths, elevation, and/or lateral locations. The spectra correspond to a period in which the samples were acquired. For each spatial location of interest, such as all the locations in a region of interest, in an image field, or other distributions, a spectrum is calculated. Spectra may be determined for only a subset of the spatial locations, such as determining the spectra for sparsely sampled locations or densely sampled locations but in a limited region.

For each receive location, a spectrum or spectra are estimated from the received signals. The spectrum is estimated by applying a Fourier transform, wavelet transform or Wigner-Ville distribution to the ultrasound samples representing each of the spatially distinct locations. Spatially distinct locations correspond to different range gates, such as different center positions, sizes or both, with or without overlap. Any transform may be applied to determine the spectrum for each of the spatially distinct locations. Each spectrum represents energy as a function of frequency (see FIG. 2).

Figure 4:
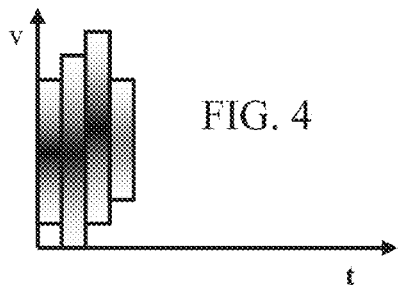
FIG. 4 is a graphical representation of an example spectral strip display.

Multiple spectra are estimated for each of the locations. FIG. 4 shows a spectral strip of spectra for a same location over time. Different spectra may be estimated for the same spatial location at different times corresponding to different periods or ensembles of acquisition. The spectrum for a given time is mapped with velocity on the horizontal axis and energy modulating the intensity. Other mapping may be used. The spectra are estimated, but may or may not be displayed.

The spectral analysis of the signals is performed separately for each of the spaced apart locations. The signals for each given location are used for spectral analysis without signals from other locations. In alternative embodiments, the signals are spatially and/or temporally filtered prior to spectral analysis, but separate spectra are provided for each location.

A set of spectra for a given time or representing the sampling period are estimated. In one embodiment, all of the spatial locations for determining spectra are sampled at a same time (e.g., same transmit and receive events). The spectra are sampled at a same time relative to a physiological cycle, such as the heart cycle. Spectra for only one period may be estimated. Spectra for the same locations are estimated for different periods to provide time varying spectral information. The samples used for estimating the spectra at a given time may be used for estimation at another time as well, such as associated with repeating estimations using a temporally moving window for selecting the samples.

In act 36, one or more characteristics of the spectra for each location are detected. Any characteristic of the spectra may be used, such as the maximum velocity, minimum velocity, mean velocity, median velocity, maximum energy, velocity associated with maximum energy, intensity, variance of velocity, range of velocity, slope or trend in the spectra, location of change of slope, shape over time, similarity to a pattern or spectra template, clutter, signal-to-noise ratio, combination of energy and velocity, or phase shift relative to known or measured cycle.

The characteristic of the spectra may be derived from one spectrum after comparison with other spectra for the location. For example, the maximum velocity over all of the spectra for a location is associated with one spectrum. A single spectrum of the spectra may be analyzed for the characteristic, such as using clutter from the first or last spectrum. The combination of spectra may be used, such as pattern matching a template of spectra with the spectra for the location.

Different types of spectral information may be useful for different diagnostic purposes. For example, the maximum velocity may more accurately indicate tissue health. The variance of the spectra may indicate flow conditions. The useful information provided in spectral strips is available for many locations at a same time, providing for selection of the spectra associated with the desired characteristics. Locating the spectrum or spectra with the maximum velocity may provide better flow information than a user guessed position.

Any now known or later developed techniques may be used to characterize or determine a characteristic of the spectra. For example, the highest velocities above a threshold level with only one or no lower velocities below the threshold indicate the maximum velocity. The maximum velocity is the highest or an average of the two or more highest velocities associated with contiguous values above the threshold or noise level in the spectrum. The signal-to-noise ratio may be calculated by measuring energy or brightness of the spectrum or spectra from samples with the transmitter turned off and samples with the transmitter active. As another example, clutter may be measured based on mapping from velocity and energy, such as high energy with low velocity indicating stronger clutter strength. Clutter may be measured by a ratio or difference of energy with and without clutter filtering.

In act 46, F-mode information is estimated from the signals. F-mode is color Doppler or other spatially distributed estimate of mean velocity, energy, and/or variance. Using the same ensemble or a sub-set of the ensemble acquired for spectral estimation, the F-mode information for the different locations is estimated. F-mode information indicates characteristics of flow, such as showing a flow region with higher and lower flow locations.

In act 38, the Doppler gate location is set. One of the locations of the constellation is selected as the Doppler gate location or the location for which spectra are to be displayed or output. More than one location may be selected, such as selecting a location on each side of a heart valve so that spectral information is provided for both locations.

The location is set based on the tracked B-mode location, the characteristics of the spectra, or the F-mode information. For B-mode tracking, the location for the tracked Doppler gate is used. As the initial location alters position, the signals from the new position are used for spectral analysis. The tracking follows a feature or structure of the patient. At different times, the signals from different coordinates represent the response of the feature. By using the signals from the tracked location over time, the resulting spectra represent the feature despite motion.

Signals from different locations are used to estimate spectra separately. As the tracked Doppler gate changes position, any new spectrum is determined for the new location. This spectrum is added to the spectral strip or spectra from a previous location or locations. Alternatively or additionally, signals from different locations may be combined into an on-going stream, such as including signals from different locations in a given ensemble for estimation of a spectrum.

For setting the Doppler gate location based on the spectra characteristics, the characteristics of the spectra for different locations are compared. For example, the best fit of a template to the spectra of the different locations is identified. As another example, the location that has the most amount of correct flow characteristics, such as velocity above a given level, and has the least amount of undesired characteristics, such as clutter, is selected. Fuzzy logic, mapping, weighted averaging or other logic may be used to combine the values for different characteristics to select one location. Alternatively, the best gate location may just be the location with the highest signal-to-noise ratio for high velocity signals while discounting gates with strong clutter signals.

In another approach, the Doppler gate location is set using F-mode information. The location associated with a center of gravity or geometric center of a largest region of flow is identified. Flow characteristics associated with a valve or other object may be identified and used to set the location. The location associated with a greatest velocity, energy, variance, or combination thereof may be used.

In one embodiment, the Doppler gate location is set based on a combination of approaches. Any combination of two or three of the B-mode, spectral analysis, and F-mode approaches may be used. Other approaches may be used in combination with one, two or all three of the B-mode, spectral analysis, and F-mode approaches. The combination may be by averaging locations output by each approach. The combination may be by selecting a location output by the different approaches based on a criterion, such as the location most similar to the other output locations (e.g., the middle location from three possibilities).

In one embodiment, the combination is a provisional setting by one approach and then refining using another approach. For example, the B-mode information is used for tracking the initial Doppler gate. The tracking is used to establish the constellation of locations (see act 40 below). The multi-gate constellation is acquired, and the spectral analysis is used to select the Doppler gate location from the constellation. The tracking is then performed based on the selected Doppler gate location in a repetition of the process. This allows the possibility that the optimal gate position may be time varying throughout the heart cycle.

In another example combination, the B-mode tracking is refined based on the F-mode information. The B-mode tracking indicates the location of the constellation. The F-mode information for the tracked constellation is used to set the Doppler gate location, such as at the center of the detected flow. Complex flow profiles found in diseased valves, such as due to calcification, may have both positive and negative flow (i.e., flow towards and away from the transducer). F-mode information may be used to properly place the Doppler gate as desired in complex flow profiles.

In act 42, the spectra for the positioned Doppler gate are selected or estimated. The location or locations set in act 38 define the signals used for spectral Doppler. As the locations vary over time, the signals used for the spectral Doppler are based on the old, new or old and new locations. Where the spectra are already estimated, such as in act 34, the spectra may be selected (e.g., loaded from memory). Alternatively, the spectra are calculated again with the same or different estimation settings (e.g., flow sample count or ensemble size or with samples from a combination of locations being used in one ensemble). Where the spectra have not been previously estimated for setting the Doppler gate location, estimation is performed.

In act 44, an image is displayed. The image is a function of at least one of the spectra for the plurality of spatially distinct locations. The spectra are used to provide information to the user. The image may provide information associated with only one spectrum in other embodiments.

In one embodiment, a spectral strip for the Doppler gate location is displayed. FIG. 4 shows an example spectral strip display simplified for illustration. The spectral strip shows the frequency modulated by energy as a function of time. Any now known or later developed spectral strip mapping may be used, such as gray scale mapping with the intensity representing energy. Filtering may be applied to smooth the spectrum. Characteristics of the spectral strip may be determined and displayed, such as graphically tracking a maximum velocity as a function of time in the spectral strip.

Since the location or coordinates for the Doppler gate may change over time, the spectral strip is generated from signals for different locations. Different ones of the spectra may be estimated from signals for different locations. A given spectrum may be estimated from signals from different locations. As the Doppler gate position is set to different locations at different times, the spectral strip is displayed in an on-going manner as if representing a given Doppler gate location.

Multiple strips may be displayed. For example, spectral strips for two or more selected locations are output for comparison. Each of the multiple selected Doppler gate locations is tracked or positioned over time. The resulting multiple spectral strips provide spectra for the desired feature of the patient.

In one embodiment, the spectral strip is displayed with a spatial image, such as a one-dimensional M-mode, two-dimensional B-mode, two-dimensional F-mode, or combination thereof image. The image is of the region of interest using data acquired for PW Doppler sampling. The location of the selected spectrum or spectra may be indicated graphically in the image, such as represented by the circle in the region of interest of the field of view shown in FIGS. 5 and 6. For example, text, color, symbol, or other indicator shows the user the location for the automatically determined range gate corresponding to the selected spectrum. Where multiple spectra are displayed, matched color coding between the acquisition range gates and displayed spectra may be used. For example, the indication of the location of the range gate uses orange. The corresponding spectrum is shaded in orange, outlined in orange, or otherwise labeled in orange. Other indications may be used, such as text labels or numbering.

In act 40, acts 26 and 28 are updated based on the setting of the position of the Doppler gate. As the Doppler gate changes to different coordinates due to movement, the acquisition of data is changed.

In one embodiment, the transmit beam and/or receive beam position is changed to be centered on the Doppler gate location. Any characteristic of the beam position may be set, such as the scan line origin, scan line angle, or focus. For example, the scan line angle is changed laterally or in elevation to cover the set Doppler gate. The transmit beam may cover multiple lateral and elevation locations. Since the energy may be stronger at the center of the transmit beam, the center or scan line of the transmit beam is changed to cover the current location of the Doppler gate. A receive beam is similarly positioned to intersect with the current location of the set Doppler gate.

The focus may be changed to the Doppler gate. Where the Doppler gate is at a different depth, the focus is changed to the different depth.

Other characteristics of the beams may change by location. For example, the transmit beam may be made wider or narrower. The F#, apodization, or aperture may vary based on the location.

The updating of the beams may provide stronger signal-to-noise ratio for the Doppler gate location than for other locations. Since the Doppler gate is used to output information, a stronger signal-to-noise ratio is desired. Other locations are still sampled for positioning the Doppler gate. In alternative embodiments, the beams do not change based on the setting of the Doppler gate.

Figure 5:
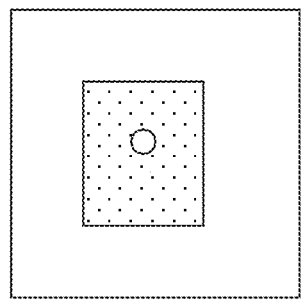
FIG. 5 is a graphical representation of an example constellation of sample locations and a Doppler gate location in a region of interest at one time.
Figure 6:
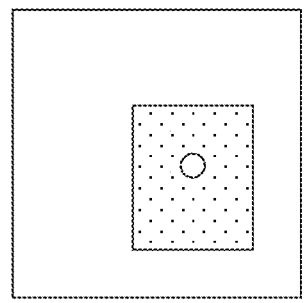
FIG. 6 is a graphical representation of the example constellation of the sample locations and the Doppler gate location of FIG. 5, but tracked to a different location for a different time.

In another embodiment, the constellation of spaced apart locations is established based on the set Doppler gate. The spatial sampling is for positioning the Doppler gate. Given a previous Doppler gate, the spatial sampling is centered on the Doppler gate for optimizing the setting of future gate locations. FIG. 5 shows a constellation of a region of interest represented by dots in a box. The constellation is centered on the Doppler gate, located at the circle. Other locations than the center may be keyed to the Doppler gate. The sampling distribution or constellation is updated over time to be centered at the set Doppler gate. As the Doppler gate changes, the locations sampled also changes. FIG. 6 shows the location of the Doppler gate changing coordinates relative to the field of view. The constellation also changes. In alternative embodiment, the sampled locations are static or do not change based on the setting.

The sampling distribution may change based on the change in the beams. As the beams change location, the sampling locations likewise change. In other embodiments, the sampling locations change while the beams are maintained or vice versa.

Small excursions in the optimal Doppler gate position may not trigger a change in the acquisition of the signals. For example, the change in position of the Doppler gate is compared to a threshold. Changes by one or two location widths (or other distances) in the sampling distribution do not trigger change in the acquisition, but larger changes do trigger change.

The movement or change in the Doppler gate position may be used for other purposes. The process or acts 26-46 is ongoing based on an initial setting of the Doppler gate. As motion occurs, the Doppler gate position is updated. For large, rapid motion, the setting may not perform as desired. In response to detecting a sufficiently large (above a threshold amount) motion, the process may be reinitiated. The Doppler gate is again set manually or initially before tracking or other setting update of the Doppler gate position. Gate placement is performed without the B-mode tracking, F-mode setting, or spectral analysis. For example, if the signal from the constellation is completely lost or the tracking based on B-mode is determined to be far off track (e.g., highest similarity is below a threshold), the system triggers a return to B-mode and/or F-mode acquisition (i.e., interleaved with or without PW Doppler acquisition) for an interval. The interleaved B-mode or F-mode scanning allows a new gate constellation position to be determined via image based techniques or manually. This triggering may alternatively or additionally be based on an ECG waveform, so that the acquisition needed for the position analysis is performed at a known part of the cardiac cycle.

Figure 7:
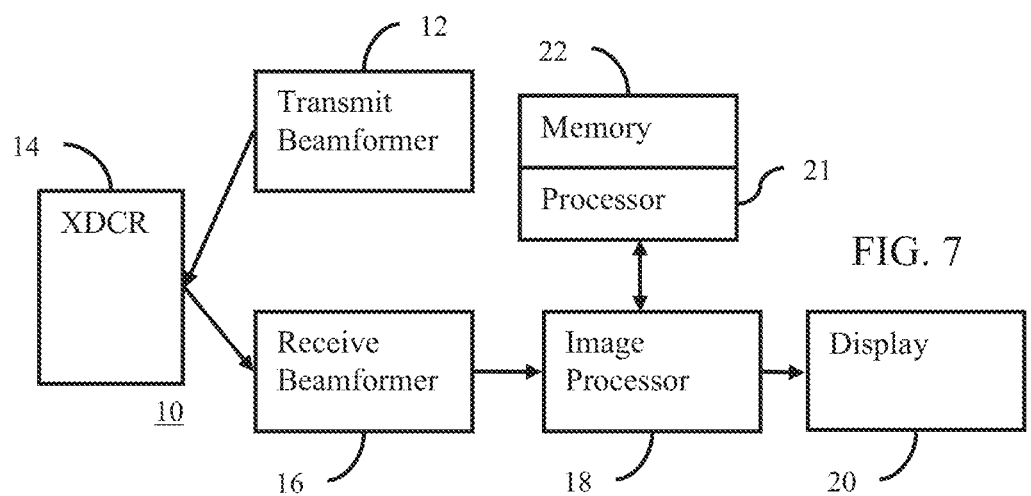
FIG. 7 is a block diagram of one embodiment of a system for positioning a Doppler gate in spectral Doppler ultrasound imaging.

FIG. 7 shows a system 10 for positioning a Doppler gate in spectral Doppler ultrasound imaging. The system 10 is a medical diagnostic ultrasound imaging system, but other imaging systems may be used, such as a workstation. The system 10 estimates spectra for a Doppler gate location and positions the Doppler gate location over time based on PW sampling without interleaving for B-mode or F-mode specific acquisition. The system 10 centers a constellation of sample locations and centers a transmit and/or receive beams on the Doppler gate. As the Doppler gate is set to a different location due to motion, the constellation and beam centers are repositioned.

The system 10 includes a transmit beamformer 12, a transducer 14, a receive beamformer 16, an image processor 18, a display 20, and a memory 22. Additional, different or fewer components may be provided, such as the system 10 without the front-end beamformers 12, 16 and transducer 14 or the system 10 with a scan converter.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two, or three-dimensional region. Vector®, sector, linear or other scan formats may be used.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, and combinations thereof.

The transmit beamformer 12 is operable to transmit one or more transmit beams of ultrasound energy substantially simultaneously. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The transmit beam substantially covers a wide region, such as being divergent, a plane wave, collimated, unfocussed, weakly focused, or focused to cover multiple receive lines. "Substantially" accounts for sufficient acoustic energy to provide echoes and imaging above noise. In one embodiment, the transmit beam is sufficiently wide to cover up to 64 receive beams or scan lines distributed in a column (e.g., 8×8), a plane (1×64), or other arrangements (e.g., 4×16). By controlling the apodization, aperture, and delay profile, different size regions may be scanned with a given transmit beam.

The transmit beamformer 12 may generate multiple or split beams. The split beams are formed for pulsed wave spectral Doppler estimation for two regions substantially simultaneously. In alternative embodiments, a single transmit beam is formed for each transmit event.

For split beams, more than one transmit beam is generated substantially simultaneously. For example, a transmit beam is generated with a grating lobe. The focus, apodization, aperture (e.g., discontinuous selection of elements), or other characteristic is set to cause a grating lobe at sufficient amplitude for generating echoes above any noise. A high amplitude transmit beam may be steered at an angle away from normal to the array to generate the grating lobe. Samples are received in response to the primary beam and the grating lobe. As another example, the transducer array is divided into two or more apertures. The separate apertures are used to form the different transmit beams. In another example, frequency or other coding is used. For yet another example, the same aperture is used to transmit multiple beams by combining delayed waveforms for both beams at each element. Combinations of these examples may be provided.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used. For example, the receive beamformer 16 has sufficient processing power and/or hardware components to substantially simultaneously form 64 or other number of receive beams in response to a same transmit. Parallel and/or sequential processing may be used to form different beams. Parallel beamforming may be provided without storing ultrasound samples for each element for an entire receive event in a memory. Alternatively, a memory may be used to store the ultrasound samples for each element.

The receive beamformer 16 is configured into a plurality of channels for receiving electrical signals representing echoes or acoustic energy impinging on the transducer 14. A channel from each of the elements of the receive aperture within the transducer 14 connects to an amplifier for applying apodization amplification. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. The summer sums the relatively delayed and apodized channel information together to form a beam. In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

For parallel receive operations, different delays, apodization, and summing are provided for the different beams. For split or multi-transmit beam, equal or different numbers of parallel beamforming are used for each beam. For example, two transmit beams are formed. Thirty two receive beams are formed for each of the two transmit beams. As another example, eight receive beams are formed from one transmit beam and twenty four receive beams are formed from another transmit beam.

Beamforming parameters including a receive aperture (e.g., the number of elements and which elements used for receive processing), the apodization profile, a delay profile, a phase profile, imaging frequency, inverse coding, and combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated in response to each transmit beam. For example, up to 64 or other number of receive beams are formed in response to one transmit beam. Each receive beam is laterally and/or elevationally spaced in two or three-dimensions from other receive beams, so samples are acquired for locations along different scan lines.

Acoustic echoes are received by the transducer 14 in response to the transmit beam. The echoes are converted into electrical signals by the transducer 14, and the receive beamformer 16 forms the receive beams from the electrical signals. The receive beams are collinear, parallel and offset or non-parallel with the corresponding transmit beam. The receive beams may be adjusted to account for spatial two-way differences, such as adjusting the delay profile and/or amplitude differently for receive beams closer to the transmit beam center than for receive beams spaced further from the transmit beam center. Alternatively, a single receive beam is generated for each transmit beam.

The receive beamformer 16 outputs data representing different spatial locations of a scanned region. The receive beamformer 16 generates samples at different depths along each receive beam. Using dynamic focusing, samples are formed for different depths. By using different receive beams and scan lines, samples are formed from two- or three-dimensional distribution of locations. The ultrasound data is coherent (i.e., maintained phase information), but may include incoherent data.

Figure 2:
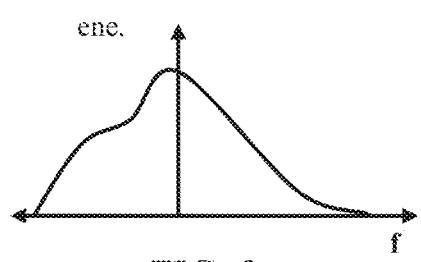
FIG. 2 is a graphical representation of an example spectrum.

The image processor 18 includes a spectral Doppler processor and/or imaging detectors. In one embodiment, the image processor 18 is a digital signal processor or other device for applying a transform to the receive beam data. A sequence of transmit and receive events is performed over a period. A buffer or the memory 22 stores the receive beamformed data from each transmit and receive event. Any pulse repetition interval may be used for the transmit beams. Any number of transmit and receive events may be used for determining a spectrum, such as three or more. The image processor 20 estimates a spectrum for each of the different locations (e.g., each of the depths of each of the receive beams in a region of interest). By applying a discrete or fast Fourier transform, or other transform, to the ultrasound samples for the same spatial location, the spectrum representing response from the location is determined. A histogram or data representing the energy level at different frequencies for the period of time to acquire the samples is obtained. FIG. 2 shows one example spectrum for a spatial location.

By repeating the process, the image processor 20 may obtain different spectra for a given location at different times. Overlapping data may be used, such as calculating each spectrum with a moving window of selected ultrasound samples. Alternatively, each ultrasound sample is used for a single period and spectrum.

A spectrum may be determined for each of a plurality of spatial locations, such as for over 200 depths on each of 64 or other number of receive beams. The data for each location is transformed. The image processor 18 may include a plurality of components for parallel processing or a single component for parallel or sequential estimation.

The image processor 18 may derive information from a given spectrum or from a plurality of spectra. In one embodiment, the image processor 18 determines a clutter level, signal-to-noise ratio, maximum velocity, velocity range, and/or other characteristics. By determining a maximum velocity or other characteristic of each spectrum, locations associated with motion or flow may be identified. An optimal location for the Doppler gate is identified.

The image processor 18 may include a B-mode detector for determining intensity from samples acquired for spectral Doppler. The image processor 18 may include a correlation processor or other color Doppler detector for determining average velocity, variance, and/or energy from the samples acquired for spectral Doppler. One or more filters, such as clutter, spatial or temporal filters may be provided.

The detector outputs incoherent image data. Additional processes, such as filtering, interpolation, and/or scan conversion, may be provided by the image processor 18.

A processor 21 is provided. The processor 21 may be part of the image processor 18. The processor or processors used for estimation or detection control the imaging and/or system 10. The processor 21 is a general processor, control processor, digital signal processor, application specific integrated circuit, field programmable gate array, graphics processing unit, analog circuit, digital circuit, combinations thereof or other now known or later developed device for processing. The processor 21 is configured by hardware, software, or both to perform and/or cause performance of various acts, such as the acts discussed above for FIG. 1.

The processor 21 is configured to set a location of the Doppler gate as a function of the sampled receive beams. The samples are acquired for spectral analysis at different locations. Without interleaving for separate scanning in other modes, the samples for spectral Doppler may also be used for B-mode and/or F-mode detection. Alternatively, B-mode and F-mode detection are not performed and the location is set based on spectral analysis.

Using B-mode information, F-mode information, spectral Doppler information, or combinations thereof, the location of the Doppler gate for a given time or period is set. The location may be updated. To keep the gate location at the desired feature, the setting of the gate location is repeated. The processor 21 repeats setting of the gate location.

The processor 21 may control the beamformers 12, 16. The beams and sampling may be centered on the Doppler gate location. As the gate location changes, the beamformers 12, 16 are controlled to change the sampling and beams. By positioning a center of the distribution of locations, the processor 18 provides for more accurate setting of the gate location for later times. By positioning a center and/or focus of the transmit beam on the gate location, the signals for spectral analysis may have better signal-to-noise ratio than for other locations. The center of the beam and focus represent regions of greater energy. The processor 21 controls the beamformers 12, 16 to change the lateral, elevation, and focus of the transmit and receive beams for centering one of the transmit beams and/or the distribution of locations on the set Doppler gate location.

The image processor 18 generates display values as a function of the spectra estimated for the Doppler gate location. Display values include intensity or other values to be converted for display, values provided to the display 20 (e.g., red, green, blue values), or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values are generated for a spectral strip display.

The display 18 is a CRT, monitor, LCD, plasma screen, projector or other now known or later developed display for displaying an image responsive to the display values. For a grey scale spectral Doppler image, a range of velocities with each velocity modulated as a function of energy is provided as a function of time. The selected spectrum indicates the velocity and energy information for a given time. The intensity of a given pixel or pixel region represents energy where velocity is provided on the vertical scale and time provided on the horizontal scale. Other image configurations may be provided, including colorized spectral Doppler images.

The memory 22 stores buffered data, such as ultrasound samples for spectrum estimation. The memory 22 may store location information, B-mode information, F-mode information, spectra, characteristics of spectra, display values or images, such as a CINE memory, or other information.

In one embodiment, the memory 22 is a non-transitory computer readable storage medium having stored therein data representing instructions executable by the programmed processor 18 for positioning a Doppler gate in spectral Doppler ultrasound imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for positioning a Doppler gate in spectral Doppler ultrasound imaging, the method comprising:
   transmitting repetitively, from a transducer array, transmit beams;
   receiving, repetitively in response to the transmitting, signals from different receive locations;
   generating B-mode information representing the different receive locations at different times from at least some of the signals;
   tracking the Doppler gate location with the B-mode information;
   estimating a first spectrum for the Doppler gate location from the signals for the tracked Doppler gate location; and
   displaying an image, the image being a function of the first spectrum.

2. The method of claim 1 wherein tracking comprises detecting a change of the Doppler gate location from a first location at a first time to a second location at a second time, wherein estimating comprises estimating from the signals for the second location;
   further comprising estimating a second spectrum for the Doppler gate location from the signals for the first location; and
   wherein displaying comprises displaying the image as a function of the first and second spectra representing the Doppler gate location from the different times.

3. The method of claim 1 wherein transmitting comprises transmitting simultaneously the beams from different apertures of the transducer array to laterally spaced apart scan lines and applying separate delay patterns to the different apertures.

4. The method of claim 1 wherein receiving comprises forming a plurality of receive beams in response to each of the transmit beams, and obtaining the signals for additional receive locations corresponding to the receive beams, respectively, such that the signals for the different receive locations and the additional receive locations are obtained substantially simultaneously.

5. The method of claim 1 wherein estimating comprises applying a Fourier transform to the signals representing the Doppler gate location, the first spectrum comprising energy as a function of frequency.

6. The method of claim 1 wherein generating the B-mode information comprises detecting intensity from single samples of the signals for the different receive locations for each of the different times, and wherein estimating comprises estimating from a plurality of the signals for the tracked Doppler gate location, the plurality including one of the single samples.

7. The method of claim 1 wherein tracking comprises determining a translation with a greatest similarity between the B-mode information of the different times, the tracked Doppler gate location corresponding to the Doppler gate location shifted by the translation.

8. The method of claim 1 wherein displaying comprises displaying a spectral strip with the spectra being for the Doppler gate at different locations as tracked over time.

9. The method of claim 1 further comprising:
   adjusting a transmit focus of the transmitting over time to the tracked Doppler location.

10. The method of claim 1 further comprising:
    adjusting a lateral and elevation position of the beams to the tracked Doppler gate location.

11. The method of claim 1 further comprising:
    estimating F-mode information from the signals; and
    refining the tracking based on the F-mode information.

12. In a non-transitory computer readable storage medium having stored therein data representing instructions executable by a programmed processor for positioning a Doppler gate in spectral Doppler ultrasound imaging, the storage medium comprising instructions for:
    receiving signals over time for each a plurality of spaced apart locations;
    performing spectral analysis of the signals separately for each of the spaced apart locations, the spectral analysis providing spectra for each of the spaced apart locations;
    detecting a characteristic of each spectrum from the spaced apart locations;
    setting a Doppler gate location to one of the spaced apart locations as a function of the characteristic of each spectrum;
    updating a distribution of the spaced apart locations as a function of the set Doppler gate location so that a center of the distribution is at the set Doppler gate location.

13. The non-transitory computer readable storage medium of claim 12 wherein receiving comprises receiving for a constellation of possible Doppler gate locations in response to multiple simultaneous transmit beams.

14. The non-transitory computer readable storage medium of claim 12 wherein performing spectral analysis comprises generating a spectral strip for each of the spaced apart locations.

15. The non-transitory computer readable storage medium of claim 12 wherein detecting comprises detecting a velocity range, shape over time, intensity, energy relative to velocity, or combinations thereof as the characteristic.

16. The non-transitory computer readable storage medium of claim 12 wherein detecting comprises detecting a signal-to-noise ratio and clutter strength as the characteristic.

17. The non-transitory computer readable storage medium of claim 12 further comprising:
    updating a transmit beam position to be centered at the set Doppler gate location.

18. The non-transitory computer readable storage medium of claim 12 further comprising:
    detecting movement above a threshold; and
    initiating gate placement without detection of the characteristic.

19. The non-transitory computer readable storage medium of claim 12 further comprising:
    generating B-mode information from pulse wave signals;
    tracking a region for the Doppler gate location with the B-mode information; and
    establishing the spaced apart locations based on the tracking.

20. In a non-transitory computer readable storage medium having stored therein data representing instructions executable by a programmed processor for positioning a Doppler gate in spectral Doppler ultrasound imaging, the storage medium comprising instructions for:
    receiving signals over time for each a plurality of spaced apart locations;
    detecting B-mode information for different times from at least some of the signals;
    tracking a location over time with the B-mode information;
    updating the spaced apart locations as a function of the tracked location;

performing spectral analysis of the signals separately for each of the spaced apart locations, the spectral analysis providing spectra for each of the spaced apart locations;
detecting a characteristic of each spectra from the spaced apart locations; and
setting a Doppler gate location to one of the spaced apart locations as a function of the characteristic of each spectrum.

* * * * *